(12) United States Patent
Reznick

(10) Patent No.: US 8,517,934 B2
(45) Date of Patent: Aug. 27, 2013

(54) CUSTOMIZABLE, SELF HOLDING, SPACE RETRACTING ARTHROSCOPIC/ENDOSCOPIC CANNULA SYSTEM

(71) Applicant: Alan M. Reznick, Woodbridge, CT (US)

(72) Inventor: Alan M. Reznick, Woodbridge, CT (US)

(*) Notice: Subject to any disclaimer, the term of this patent is extended or adjusted under 35 U.S.C. 154(b) by 0 days.

(21) Appl. No.: 13/706,677

(22) Filed: Dec. 6, 2012

(65) Prior Publication Data

US 2013/0096388 A1  Apr. 18, 2013

Related U.S. Application Data

(62) Division of application No. 12/662,952, filed on May 13, 2010.

(60) Provisional application No. 61/272,089, filed on Aug. 14, 2009.

(51) Int. Cl.
*A61B 1/32* (2006.01)

(52) U.S. Cl.
USPC ........... 600/227; 600/206; 600/210; 600/214; 600/217; 600/235

(58) Field of Classification Search
USPC ............... 600/206, 210, 214, 217, 227, 235; 604/174, 104, 164.04, 164.05
See application file for complete search history.

(56) References Cited

U.S. PATENT DOCUMENTS

| | | | |
|---|---|---|---|
| 4,043,346 A | 8/1977 | Mobley et al. | |
| 4,393,872 A | 7/1983 | Reznik et al. | |
| 5,186,168 A | 2/1993 | Spofford et al. | |
| 5,226,890 A | 7/1993 | Ianniruberto et al. | |
| 5,273,026 A | 12/1993 | Wilk | |
| 5,411,517 A | 5/1995 | Guignard | |
| 5,478,329 A | 12/1995 | Ternamian | |
| 5,630,805 A | 5/1997 | Ternamian | |
| 5,817,062 A | 10/1998 | Flom et al. | |
| 5,865,802 A | 2/1999 | Yoon et al. | |
| 6,165,180 A | 12/2000 | Cigaina et al. | |
| 6,325,812 B1 | 12/2001 | Dubrul et al. | |
| 6,451,024 B1 | 9/2002 | Thompson et al. | |
| 6,482,178 B1 | 11/2002 | Andrews et al. | |
| 6,589,213 B2 | 7/2003 | Reydel | |

(Continued)

*Primary Examiner* — Andrew Yang
*Assistant Examiner* — Olivia C Chang
(74) *Attorney, Agent, or Firm* — Welsh Flaxman & Gitler LLC

(57) ABSTRACT

The present invention is directed to a device including an inner cannula having one or more wings or leaflets attached to one end thereof. The wings or leaflets can be cut to length or shaped to facilitate holding the operative field open for optimal visualization and the use of surgical instruments. A shorter, outer cannula is fitted over the inner cannula and a flange attached to the outer cannula is moved from a closed position in which the wings are covered by the inner surface of the cannula or to an open, deployed position in which the wings are opened. The outer cannula may be textured or shaped to aid in holding the desired position. The device also includes a dam or barrier at the end or other convenient location in the inner cannula to control the flow of air or fluids in the cannula as to make it useful in arthroscopic or endoscopic surgery of all types. The wings or leaflets can have mating tapered tips that joint into a single tip when closed or an optional trocar to ease insertion into the desired body cavity. The design allows for manufacture at almost any size to make the device useful in the widest of surgical applications and in all joint or body cavities large or small.

4 Claims, 6 Drawing Sheets

(56) References Cited

U.S. PATENT DOCUMENTS

| | | |
|---|---|---|
| 6,626,859 B2 | 9/2003 | von Segesser |
| 6,638,265 B1 | 10/2003 | Ternamian |
| 6,843,795 B1 | 1/2005 | Houser et al. |
| 7,024,749 B2 | 4/2006 | Sagstetter |
| 7,377,897 B1 | 5/2008 | Kunkel |
| 2004/0199121 A1 | 10/2004 | Wenchell et al. |
| 2005/0240259 A1 | 10/2005 | Sisken et al. |
| 2008/0086165 A1 | 4/2008 | Lyon et al. |
| 2008/0242930 A1 | 10/2008 | Hanypsiak et al. |
| 2009/0069790 A1 | 3/2009 | Yokley et al. |

CUSTOMIZABLE, SELF HOLDING, SPACE RETRACTING ARTHROSCOPIC/ENDOSCOPIC CANNULA SYSTEM

CROSS-REFERENCE TO RELATED APPLICATIONS

The present application is a division of U.S. patent application Ser. No. 12/662,952 filed May 13, 2010, entitled "CUSTOMIZABLE, SELF HOLDING, SPACE RETRACTING ARTHROSCOPIC/ENDOSCOPIC CANNULA SYSTEM, which is currently pending, which claims the benefit of provisional patent application Ser. No. 61/272,089, filed on Aug. 14, 2009 and is incorporated by reference herein.

FIELD OF THE INVENTION

The present invention is directed to a cannula used for a multitude of medical and surgical procedures.

BACKGROUND OF THE INVENTION

During arthroscopic surgery there is a well established need for cannulae for a wide variety of procedures. These include, but are not limited to procedures in all of the joints treated by arthroscopic techniques. To meet this need, there are a number of cannulae available with a number of differing designs to control fluid flow, prevent slippage of the cannula and allow passage of instruments, sutures, implants, anchors or fiber-optic devices to and from the site of the procedure. In the past a design feature with expandable wings that engage the subcutaneous tissues to help hold the cannula in place has been developed. Unfortunately these wings are often larger than the space available in various locations of the body, such as joints and are not suited to be used in small spaces in the body. These prior art devices cannot accommodate the shape of the individual joint spaces. Further, these prior art mechanisms require a recess from the tip of the cannula, or a weakness of the attachment for its functionality, such as described in U.S. Pat. No. 6,325,812, issued to Dubrul. Furthermore, the mechanical design of the hinged flaps of the prior art devices cannot be shortened or changed at the time of surgery by the surgeon to accommodate the shape of the joint or to directly aid in exposing the surgical sight of interest.

More importantly there is a current need, well known to those familiar in the advanced form of the art, for internal retraction of the soft tissue allow for a reduction of the fluid pressures required to distend or open the joint space. Such a system would allow for longer operative times and therefore allow more sophisticated and complex procedures to be completed using less fluid at a lower pressure inside a joint space to distend the joint. This would reduce the need for absolute seals at the ends of the cannula, as well as reduce the complications associated with high pressure fluid pumps as well as the resultant fluid extravasations into the local extra-articular tissues in order to keep the joint or body cavity space open. This would also decrease the risk of skin complications, loss of visualization and nerve damage in the more complex cases requiring longer operative times. The flexible wing design of the present invention would produce customizable soft tissue retractors that would service this purpose. A device with these features would increase safety with longer surgical times or more complex procedures thereby advancing the state of the art. Furthermore, there is a need in the state of the art to have a device of this type with a sufficiently simple design as to allow for inexpensive manufacture or mass production in a multitude of sizes and configurations to accommodate many differing joints or body cavities.

Therefore, with that in mind, there is a need in the current art for a self, holding cannula that could be manufactured in any size, and be customizable at the time of surgery that has the advantages outlined below.

SUMMARY OF THE INVENTION

The present invention is constructed using an inner tabular cannula inserted within a shorter outer cannula, with an outer cannula longitudinally moving with respect to the inner cannula.

The present invention overcomes the deficiencies of the prior art by providing an endoscopic/arthroscopic, surgical utility cannula having various advantages over various prior art devices and methods of use currently on the market. This is accomplished by providing a cannula having self-holding wings connected to the distal end of the inner cannula for the purpose of stabilizing the cannula in or around the operative portal while retracting the nearby soft tissues. The actual size and dimensions of the cannula would be designed based upon the particular portal, joint, or other portion of the body into which the cannula would be inserted. Obviously, smaller joints could only accommodate a relatively small cannula and larger joints would require a bigger cannula. The number of wings that are provided to stabilize the cannula would be based upon the particular application. Therefore, the cannula, according to the present invention, can be provided with one or more wings. The orientation, length and spacing of the wings are not predetermined by the mechanical design which would allow for the expansion of the cannula, either by internal expansion or by the external folding of the wings. The wings can vary in size, length, shape and/or positional relationship based upon the operative portal or the joint to be treated. The present invention would include embodiments with pre-made "wings," "flaps," "leaflets" or "tabs" with differing lengths to match specific joints of the anatomy or the need of a specific procedure to be performed. The wings can be in any number of forms including curve or straight ends to allow for a number of trocar tips that can be sharp, dull, rounded or other shape to allow for ease of use for a given application. Furthermore, the wings need not be tapered. The design therefore can be produced in a multitude of configurations matching the needs of a great variety of internal body spaces or joint spaces requiring cannulation and many differing procedures.

The wings of the cannula of the present invention can be altered as many times as needed by any number of common cutting instruments available to the surgeon for the surgical procedure to create the correct fit before, or during the procedure. In particular if the device is placed and the fit is not optimal, the device can be modified on the surgical field as many times as needed to meet the demand of the procedure. The device can contain one or more conical or pyramidal shaped tips on one or more of the wings to create a tapered front when not deployed, for the purpose of easing the insertion of the cannula into the joint. The wings can contain tapered tips that mate with the trocar tip used to ease the insertion of the cannula into the joint.

The inner and outer surfaces of the cannula can be provided with any number of stops or notches to hold the cannula in an open or a closed position during use. Furthermore, the outer surface can be treated with any number of known or novel surface treatments, such as ridges, bumps, screw-like threads, spines or coatings to add in the passage or friction fit of the cannula in the soft tissue portal.

The material of the inner sleeve and wings of the cannula can be constructed from any material that can be cut by surgical cutters, scissors, scalpels or a number of surgical instruments available on the surgical field to the surgeon at the time of the procedure. Therefore, the length of the wings can be cut or adjusted by the surgeon using common surgical instruments. This enables the surgeon to produce a device to best take advantage of the present invention's benefits in a space of almost any configuration. The stabilized cannula of the present invention holds its place and the leaflets allow for a smooth transition from the cavity to the inner lumen, thereby easing the passage of sutures, fluids and surgical instruments for the desired endoscopic or arthroscopic surgical procedures. This feature would make passage of sutures, instruments, fluids, graft materials, scaffolds, biologic implants, autograft or allograft material, suture devices, knot pushers, drills, wires, pins, endoscopic or arthroscopic instruments and/or anchoring devices easier and will advance the state of the art. The pre-formed inner wings can be deployed in any desired joint space, abdominal cavity or sub-muscular space. Consequently, the deployed wings can expand the effective diameter of the end of the cannula and therefore can stabilize the cannula in position, while creating a smooth transition from the body cavity or space to the inner lumen of the cannula.

The cannula, according to the present invention, can be constructed from various materials, such as, but not limited to different types of rubber, plastics, thermoplastics, Teflon, or various other metals such as copper, aluminum or stainless steel.

As in all other cannulae, the outside surface of the outer cannula can be treated or manufactured with textured, rough, smooth, threaded, ribbed or other surface covers which would aid in holding the cannula in place during the procedure.

The cannula has a fitted trocar that accommodates the leaflets and is designed to aid cannula insertion into a joint, submuscular space or a body cavity for the purposes of arthroscopic or endoscopic surgery. The trocar would fit smoothly inside the inner cannula, providing a tip to ease incertion of the device. The separate inner trocar can lock in place to ease insertion. The trocar's tip can be any number of shapes, smooth, rounded, oblong, pointed, sharp or have a cutting edge without altering the function of the leaflets. At the same time, any number of the leaflets can be cut part way or fully without impeding the function of the inserting trocar. This allows for ease of insertion while maximizing the stabilizing quality of the invention presented in a wide variety of joint or body cavities as in, but not limited to shoulder, elbow, and ankle arthroscopic procedures.

The cannula wings would be sturdy enough so the cannula can also be inserted in a closed position, opened fully and partly backed out with wings still in a deployed position to further retract the soft tissues out of the operative field. The sturdy wings would also keep the cannula firmly in place. The curved shape of the open wings would also aid in the smooth insertion and removal of operative instruments. In this manner improve the operative view while reducing the amount of normal tissue removed during the surgical attempt to visualize the operative field.

It is a further object of this invention to provide a cannula system that can be used in any number of sizes, lengths and even opening shapes other than those used in the prior art such as a round, oval, oblong or rectangular opening. The outer end of the cannula can be open or covered with any number of flexible coverings or dams to hold fluids in while allowing passage of instruments, sutures or materials required for the desired procedure.

BRIEF DESCRIPTION OF THE DRAWINGS

The device of the present invention will be described in more detail hereinafter in conjunction with the drawings wherein:

FIG. 12b is an end view of the device shown in FIGS. 3 and 12a;

BRIEF DESCRIPTION OF THE PRESENT INVENTION

Figure 1:
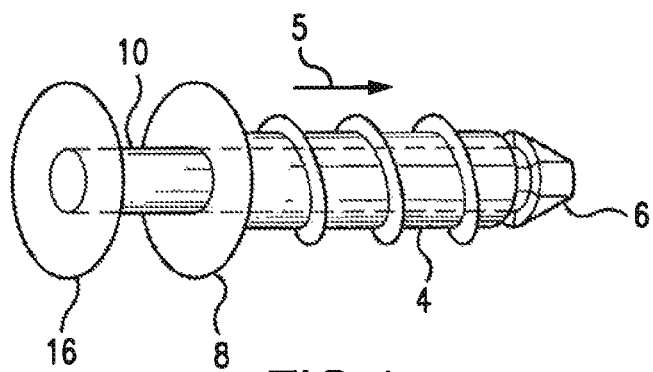
FIG. 1 is a drawing showing the cannula in the closed position with the wings provided within the cannula.
Figure 2:
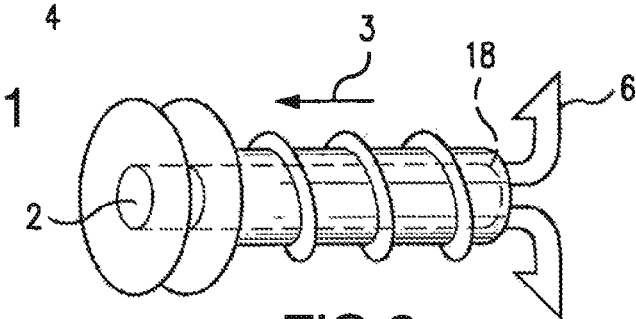
FIG. 2 is a drawing showing the cannula of FIG. 1 in an open position with the wings deployed.
Figure 5:
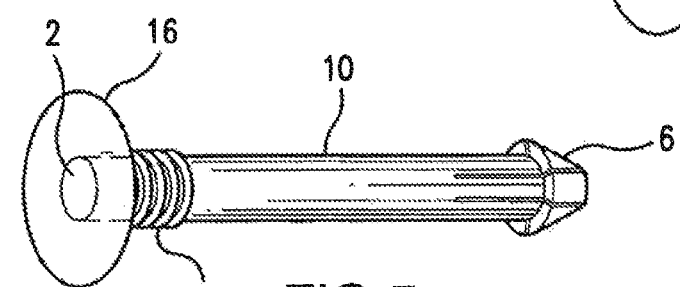
FIG. 5 is a drawing of one embodiment of the inside cannula showing the fluid dam, ridges to hold the outer cannula in the proximal position when wings are deployed.

As Illustrated in FIGS. 1-4, the cannula 1 of the present invention includes two concentric cannulae including an inner cannula 10 and an outer cannula 4 having a distal end 20, the outer cannula 4 fitting over the inner cannula 10. The inner cannula 10 is longer than the outer cannula 4 and is provided with an open flange or a water dam 2 at a proximal end of the inner cannula 10 shown in FIGS. 2 and 5. The fluid or water dam 2 could exhibit many configurations as is commonly used on prior art cannulae. The distal end of the inner cannula 10 is provided with a plurality of wings 6 as shown in FIG. 2. The number, shape and length of these wings would be based upon the particular application of the cannula. For example, FIG. 5 shows tips with partially pointed tips 6, and FIGS. 7a-7d show the use of conical tips 12. Each of the tips or wings provided on the distal end of the inner cannula, need not be equal in size, or even shape. For example, FIG. 8a has a plurality of tips or wings 6 equal in size to each other, whereas FIG. 8b illustrates wings or tips 14 shorter than wings or tips 6. As can be appreciated, the length of each of the wings or tips 6 could be of unequal size or shape to the other wings or tips.

The second, shorter outer cannula 4, as shown in FIG. 2, would be provided with a flange 8 used in a sliding motion to deploy the wings 6 to move the outer cannula 4 over the inner cannula 10, when the flange 8 is moved to the left, as depicted by arrow 3. When the flange 8 is moved to the right, as shown by arrow 5 in FIG. 1, and in cross section in FIG. 12, the wings 6 would be closed or protected within the outer cannula 4. This facilitates device insertion and removal to or from various parts of the body, such as, but not limited to joints. FIG. 2 illustrates how the wings 6 curve away from the inner lumen 18 of the inner cannula 10 making a smooth transition between the open space and the cannula lumen.

FIG. 5 illustrates an embodiment wherein the outer surface of the inner cannula 10 may be provided with various notches, ridges, rings 40 or other devices to lock the flange 8 in the open and closed positions, making the open and closed positions more obvious and apparent to the surgeon. The outer surface of the outer cannula 4 can also be provided with various threads 24 notches, ridges, rings 26 or other textures 28 to create more friction between the skin and the outer wall of the outer cannula 4 to help hold it in place. These features are illustrated in FIGS. 1-4 and FIGS. 9a, 9b and 9c. The cannula 1 can be constructed in many shapes such as round, oval, square, rectangular or many other shapes. FIGS. 10a-d illustrate some, but not all of the potential shapes.

Figure 6:
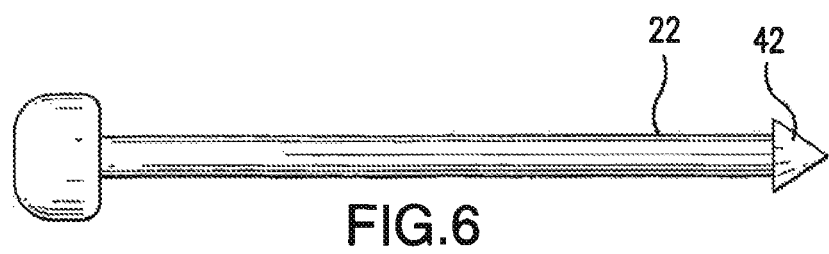
FIG. 6 is a drawing of one possible trocar shape.

FIG. 6 illustrates one possible embodiment of a standard inner trocar 22 for aid in inserting the cannula 1 into a particular location in the body. The shape of the trocar can be altered to accommodate the wing tips or not required if the conical configuration is used shown in FIGS. 7a-d. In the conical tip embodiments shown in FIGS. 7c-d, the trocar tip is built into the wing or tip design and this eliminated a component which my simplify the manufacture of the cannula and provide a cost advantage. The cannula is inserted into the body by pushing the tip 42 of the trocar against the water or fluid dam 2 when the cannula is in the closed position as shown in FIG. 1.

The wings 6 should be constructed from a material which is flexible enough to be constrained by the outer cannula 4 when it is in the closed position as shown in FIG. 1, while retaining a curved shape when it is opened as illustrated with respect to FIG. 2. The material of the wings 6 should be soft enough to be cut or shaped by scissors of any type or by any special type of cutting device available to a surgeon for operative use, such as, but not limited to, plastic, paper, foam, composite materials and/or soft metals like copper, aluminum or tin. The outer surface of each of the wings can be treated to change the holding power or friction of the wings. However, the material of the wings 6 should be firm enough to aid as a soft tissue retractor for any number of specific procedures while stabilizing the cannula position as a surgical portal allowing fluids to be introduced as well as other surgical tools. The wings 6 can be reinforced by wire, springs or various types of memory metals or other stiff material to help support their shape.

The relative orientation of the wings or tips 6 are not predetermined by the mechanical design that allows further expression of the wings or tips 6 when deployed. The wings can vary in size, length, shape and/or positioned relationship can be made for specific joints, and can be altered many times as needed during the procedure. The shape and length of each wing can be trialed tested, reshaped and retested on the operative field using common surgical instruments. The shape can also be manufactured to specifications for any of a multitude of uses.

Figure 13:
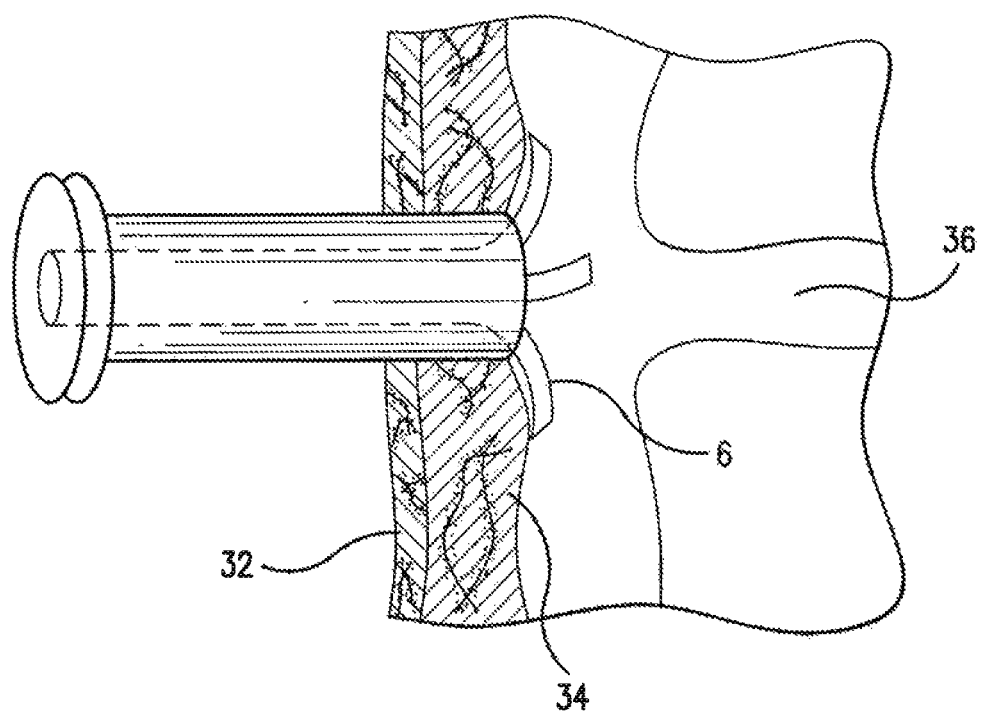
FIG. 13 is a drawing of the cannula in place through the skin, into a joint space and with wings deployed retracting the fat pad inside the joint space allowing for better visualization of the joint itself.

As shown in FIG. 13, the wings 6, by virtue of their shape, with or without customization, can act as internal retractors of the soft tissues of the body. This would facilitate more sophisticated and complex procedures. These procedures could also be completed using less fluid at a lower pressure in order to distend a joint. Operating at a lower pressure would reduce pressure related fluid extravasations into the local extra-articular tissues. This would decrease the fluid related risks of nerve damage, skin complications and loss of joint visualization in longer, more complex cases. The flexible wing design proposed here could act soft tissue retractors that would serve this purpose. If the flexible wings fit are not optimal, the device can be modified on the surgical field, with common surgical instruments, as many times as needed to meet the demand of the procedure. The wings can also be precut, premade or manufactured in varied lengths or shapes for specific procedures. The design therefore can be produced in a multitude of configurations matching the needs of a great variety of internal body spaces or joint spaces requiring cannulation and many differing procedures.

Figure 14:
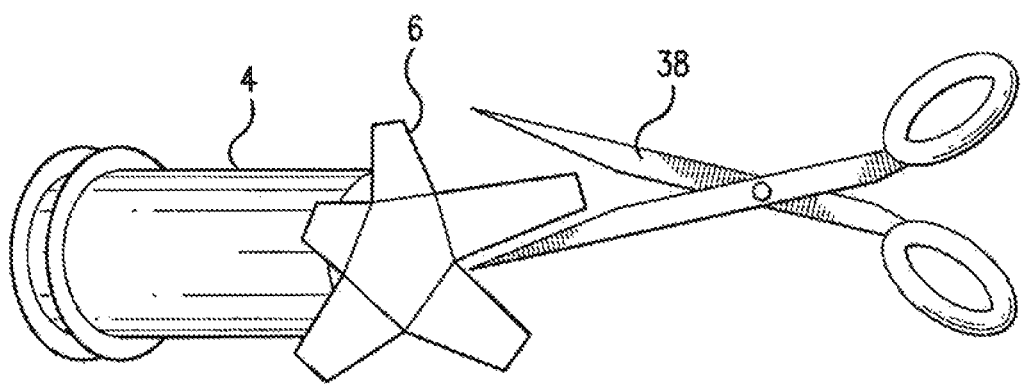
FIG. 14 is a drawing showing the manner in which the tips are shaped.

FIG. 14 illustrates the manner in which the tips or wings 6 are modified prior to or during the procedure. Generally, once the operative site is visualized, the surgeon will be able to determine the size and shape of all of the tips or wings 6. A scissor 38, or any other sharp implement would be used to cut and shape one or more of the tips or wings 6.

The device, when deployed through the skin 32, as shown in FIG. 13, is designed to hold its place in the joint space 36 while maintaining access to the desired cavity, aid in fluid flow control, prevent slippage of the cannula out of place and allow easy passage of instruments, sutures, anchors, graft materials and/or fiber-optic scope. The wings can then retract soft tissues inside the joint space such as a fat pad or synovium 34.

Figure 11A:
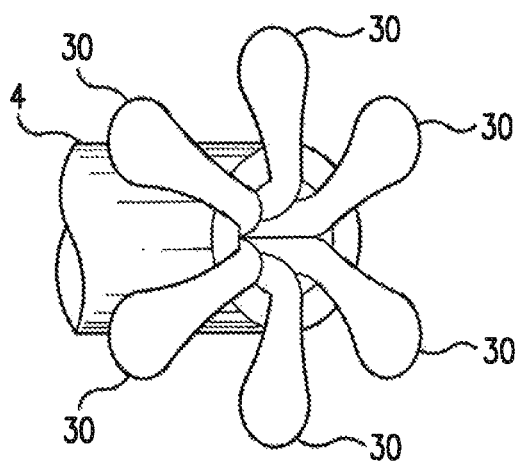
FIG. 11a is a drawing of one embodiment with a particular custom shaped wing and the custom irregular shaped wings in the deployed position.
Figure 11B:
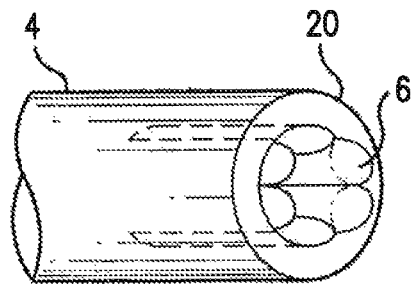
FIG. 11b is a drawing with the custom irregular shaped wings in the closed position.

FIG. 11a shows the wings 30 when they are deployed, and FIG. 11b shows the wings when they are retracted within the outer cannula. As shown in FIGS. 11a and 11b, the wings 6 can be custom made or pre-shaped 30 to accommodate the individual surgical spaces (i.e. shoulder, knee, elbow, abdomen etc.), as needed to best aid the procedure, at the time of surgery by the surgeon. If the fit is unsatisfactory, an unlimited range of changes can be made on the surgical field to fit the surgical sight of interest.

Figure 7A:
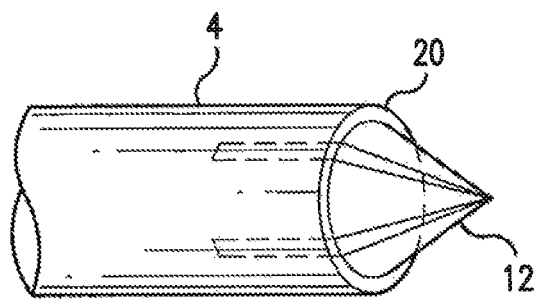
FIG. 7a is a drawing showing one embodiment the wings with mating conical/pyramidal tips in the closed position with the tips mated into one single point to ease insertion before deployment.
Figure 7B:
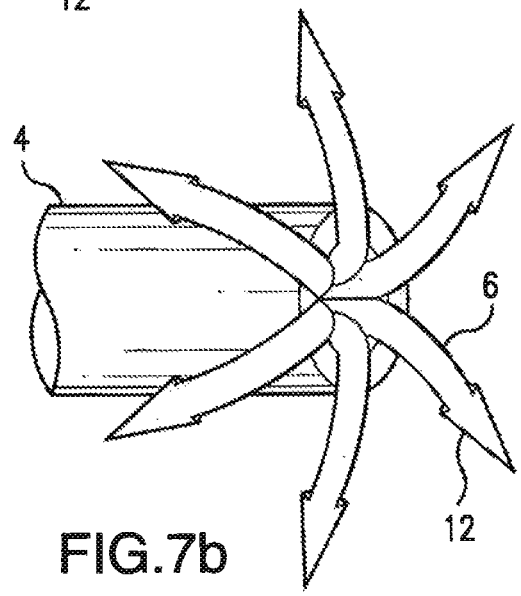
FIG. 7b shows the conical/pyramidal tips in the open position after deployment.
Figure 7C:
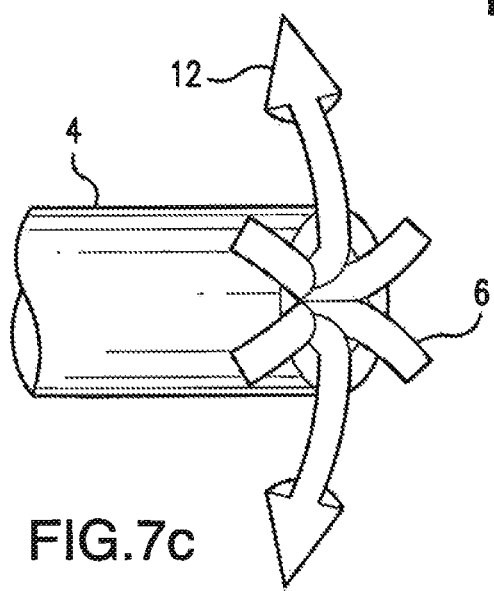
FIG. 7c shows the conical/pyramidal tips in the open position with the tapered mating tips on only two of the wings or leaflets.
Figure 7D:
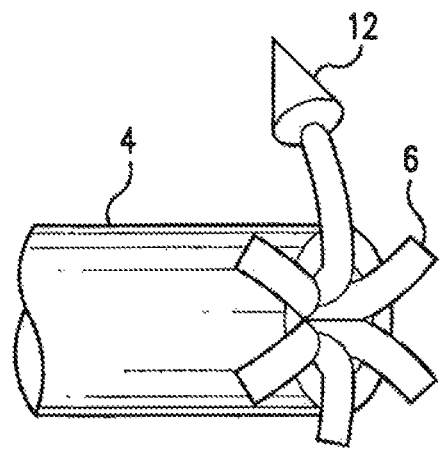
FIG. 7d shows the conical/pyramidal tip in the open position with a tapered tip only on one wing or leaflet.
Figure 8A:
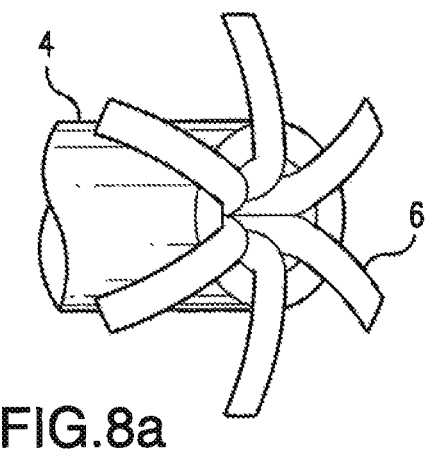
FIG. 8a shows one embodiment with equal leaflets or wings deployed without conical tips.
Figure 8B:
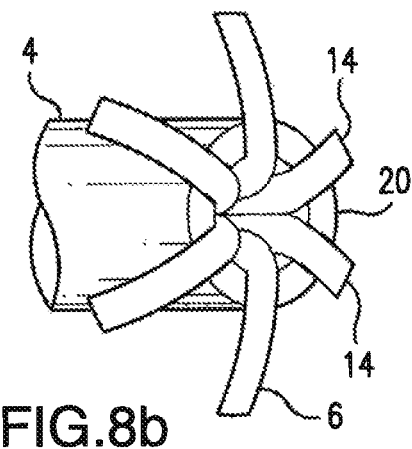
FIG. 8b is a drawing of the wings deployed with two wings cut or premade to a shorter length to accommodate a specific application or use.

FIGS. 7a-d show the use of the present invention when provided with conical tips 12 attached to one or more of the ends of the wings 6. FIG. 7a shows the cannula 1 in a closed position with the cones 12 mated and extending from the end of the inner cannula 10, but still restrained by the outer cannula 4 from being deployed. It can be appreciated that various shapes, such as a pyramidal shape, can be attached to the end of one or more of the wings 6. As illustrated in FIG. 7a, when this embodiment is in the closed position, the tips 12 would merge to a single point and allow for self-insertion into the body. The tips 12 can also act as an aid in tissue retraction, as shown in FIGS. 7b-d, when the wings or tips are fully deployed. As shown in FIGS. 7c and 7d, the cannula tips 12 need not be included on each of the wings or tips 6.

Figure 9A:
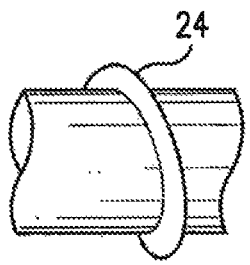
FIGS. 9a, b, and c are drawings showing various textures provided on the outer surface of the cannula.
Figure 9B:
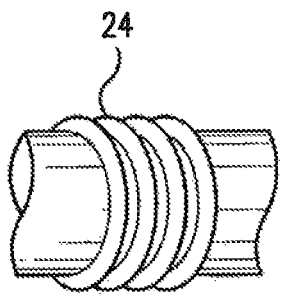
Figure 9C:
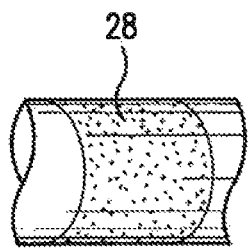
Figure 10A:
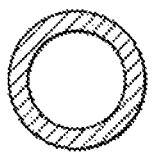
FIGS. 10a, 10b, 10c and 10d are drawings of possible embodiments with differing cross sectional shapes to accommodate different applications.
Figure 10B:
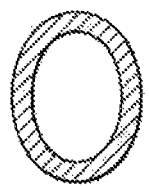
Figure 10C:
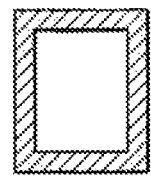
Figure 10D:
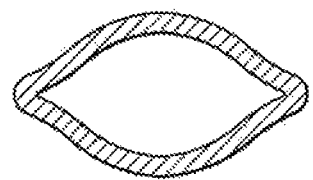

The outer surface of the outer cannula 4 can be covered with any number of surfaces, as shown in FIGS. 9a, b and c. FIG. 9a shows the use of a threaded exterior 24, 9b shows a plurality of ribs or ridges 26 extending over the entire length of the cannula 4 or a portion of the length of the cannula 4. Similarly, the outer surface of cannula 4 can be textured 28 as shown in FIG. 9c. Similar to the threaded surface 24 of FIG. 9a, the ribbed surface 26 as well as the textured surface 28 of FIG. 9c can extend part way along the cannula or along the entire length of the outer cannula 4, or for any portion or segment of that length.

Figure 3:
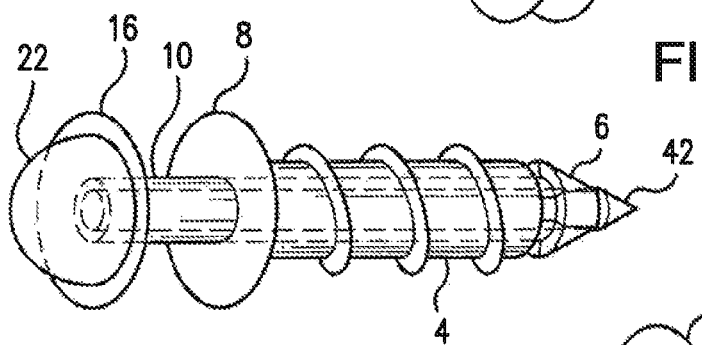
FIG. 3 is an expanded view of a cannula showing a trocar, inner and outer cannula in configuration for insertion into body cavity.
Figure 4:
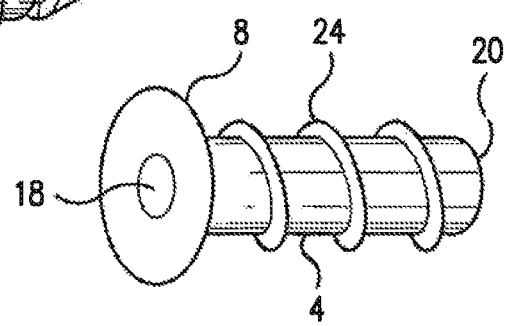
FIG. 4 is a drawing of one embodiment of the outer cannula with a threaded outside texture.
Figure 12A:
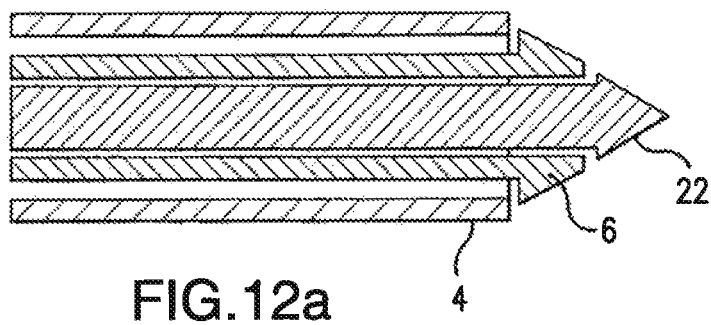
FIG. 12a is a cross-sectional view of a second embodiment of the present invention using an insertion tip being formed partly from the wings and partly from the tip of the trocar.
Figure 12B:
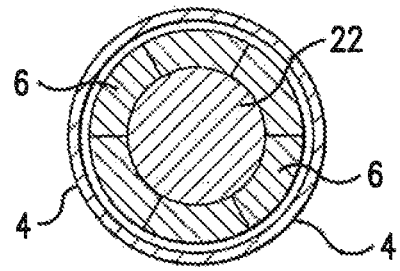

FIGS. 3 and 12 show an alternate embodiment of the present invention in which the wings have part of the trocar tip and the trocar has the balance end point. In the embodiments shown in FIGS. 3 and 12, the tips of the wings 6 mate with the edge out with a third component being an inner trocar. In this case, as shown in FIG. 8, the trimming of the wings to shape would no longer alter the trocar tip, making it easier to insert the device into the desired space. This is shown in FIG. 12 in which the tips 12 mate with the second end 20 of the outer cannula 4 and the trocar 22. In this case, the trimming of the wings to shape would no longer alter the trocar tip making it easier to insert the device into the desired space.

Both the inner cannula 10 as well as the outer cannula 4 can be constructed from any materials used in the past to construct cannulae. These materials include, but are not limited to, natural rubber, synthetic rubber, plastics, thermoplastics, Teflon® or metals, such as aluminum, copper, stainless steel, or other alloys. Based upon the field of use, the cannulae can be rigid or flexible in their totality or can exhibit rigid or flexible portions along the lengths of the cannulae 4 and 10. The cannulae could also be constructed from elastomeric material and can be fully disposable, partly reusable or rally reusable after sterilization. The elastomeric material can be provided as a coating or present throughout the cannula. The either cannula can be made of a material in the class of any of the "memory metals" or materials that change shape with the environmental temperature to facilitate use in certain body cavities or to aid in the deployment of the "wings" or "tips."

It will be appreciated by persons skilled in the art that the present invention is not limited to what has been particularly shown and described hereinabove. Rather, the scope of the present invention is defined only by the claims as follows.

What is claimed is:

1. A method of performing a surgical procedure on an individual, comprising the steps of:

a) creating an operative portal in the individual;

b) introducing a trocar within the operative portal, the trocar including a tubular outer cannula having a distal end, a proximal end and an inner surface and an outer surface, the proximal end of the tubular outer cannula; the trocar also including a tubular inner cannula having a distal end, a proximal end and an outer surface, the inner cannula being greater in length than the outer cannula, the inner cannula being positioned within the outer cannula for longitudinal movement within the outer cannula; and the trocar also includes a plurality of wings circumferentially attached to the distal end of the inner cannula, the plurality of wings retained between the inner surface of the other cannula and the outer surface of inner cannula when the outer cannula is in a first position, each of the plurality of wings angled away from the other plurality of wings enabling the plurality of wings being to stabilize the device in or around the operative portal when said outer cannula is moved to a second position with said proximal ends of both said inner and outer cannulae being adjacent to one another;

c) moving the outer cannula with respect to the inner cannula to deploy the plurality of wings;

d) visualizing the operative portal and the device with the plurality of wings deployed to determine whether the plurality of wings are adequate to stabilize the device in the operative portal;

e) moving the outer cannula with respect to the inner cannula to retain the plurality of wings between the inner and outer cannulae;

f) removing the device from the operative portal;

g) modifying the shape or size of at least one of the plurality of wings based upon the visualizing step to better stabilize the device within the operative portal;

h) reinserting the device in the operative portal;

i) moving the outer cannula with respect to the inner cannula to deploy the plurality of wings or tips to stabilize the device within the operative portal.

2. The method in accordance with claim 1, repeating steps d) through i) until the device is properly stabilized within the operative portal.

3. The method in accordance with claim 1, further comprising the step of cutting a portion of at least one of said plurality of wings or tips to modify the shape or size of at least one of said plurality of wings or tips.

4. The method in accordance with claim 3, further wherein the step for cutting a portion of at least one of said plurality of wings or tips to modify the shape or length of at least one of said plurality of tips or wings is based upon a specific joint space in the operative portal.

* * * * *

UNITED STATES PATENT AND TRADEMARK OFFICE
CERTIFICATE OF CORRECTION

| | | |
|---|---|---|
| PATENT NO. | : 8,517,934 B2 | Page 1 of 1 |
| APPLICATION NO. | : 13/706677 | |
| DATED | : August 27, 2013 | |
| INVENTOR(S) | : Alan M. Reznik | |

It is certified that error appears in the above-identified patent and that said Letters Patent is hereby corrected as shown below:

In the Claims

Column 7, line 48, through Column 8, line 37, cancel the text beginning with "1. A method of" to and ending "the operative portal", and insert the following claim:

--1. A method of performing a surgical procedure on an individual, comprising the steps of: a) creating an operative portal in the individual; b) introducing a trocar within the operative portal, the trocar including a tubular outer cannula having a distal end, a proximal end and an inner surface and an outer surface, the proximal end of the tubular outer cannula; the trocar also including a tubular inner cannula having a distal end, a proximal end and an outer surface, the inner cannula being greater in length than the outer cannula, the inner cannula being positioned within the outer cannula for longitudinal movement within the outer cannula; and the trocar also includes a plurality of wings circumferentially attached to the distal end of the inner cannula, the plurality of wings retained between the inner surface of the outer cannula and the outer surface of inner cannula when the
outer cannula is in a first position, each of the plurality of wings angled away from the other plurality of wings enabling the plurality of wings being to stabilize the device in or around the operative portal when said outer cannula is moved to a second position with said proximal ends of both said inner and outer cannulae being adjacent to one another; c) moving the outer cannula with respect to the inner cannula to deploy the plurality of wings; d) visualizing the operative portal and the device with the plurality of wings deployed to determine whether the plurality of wings are adequate to stabilize the device in the operative portal; e) moving the outer cannula with respect to the inner cannula to retain the plurality of wings between the inner and outer cannulae; f) removing the device from the operative portal; g) modifying the shape or size of at least one of the plurality of wings based upon the visualizing step to better stabilize the device within the operative portal; h) reinserting the
device in the operative portal; i) moving the outer cannula with respect to the inner cannula to deploy the plurality of wings or tips to stabilize the device within the operative portal.--

Signed and Sealed this
Thirty-first Day of December, 2013

Margaret A. Focarino
*Commissioner for Patents of the United States Patent and Trademark Office*